US00PP17958P2

(12) United States Plant Patent
Hammond

(10) Patent No.: US PP17,958 P2
(45) Date of Patent: Aug. 28, 2007

(54) ***ARGYRANTHEMUM* PLANT NAMED 'M905'**

(50) Latin Name: *Argyranthemum frutescens*
Varietal Denomination: M905

(76) Inventor: Frank Hammond, 100 Boundary Road, Narre Warren East, 3804 Victoria (AU)

( * ) Notice: Subject to any disclaimer, the term of this patent is extended or adjusted under 35 U.S.C. 154(b) by 0 days.

(21) Appl. No.: 11/349,688

(22) Filed: Feb. 7, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Argyranthemum* plant named 'M905', characterized by its compact, upright and rounded plant habit; freely branching habit; dense and bushy plants; freely flowering habit with numerous inflorescences per plant; and anemone-type inflorescences with pink-colored ray florets and golden yellow-colored disc florets.

1 Drawing Sheet

Botanical designation: *Argyranthemum frutescens.*
Cultivar denomination: 'M905'.

BACKGROUND OF THE INVENTION

The present invention relates to a new and distinct cultivar of *Argyranthemum* plant, botanically known as *Argyranthemum frutescens* and hereinafter referred to by the cultivar name 'M905'.

The new *Argyranthemum* originated from an open-pollination in 1999 of a proprietary seedling selection of *Argyranthemum frutescens* identified as M2/16, not patented, as the female, or seed, parent with an unidentified seedling selection of *Argyranthemum frutescens,* as the male, or pollen, parent. The cultivar M905 was discovered and selected by the Inventor as a flowering plant within the progeny from the aforementioned open-pollination in a controlled environment in Narre Warren East, Victoria, Australia on Nov. 15, 1999.

Asexual reproduction of the new *Argyranthemum* by terminal cuttings in a controlled environment since November, 1999, in Narre Warren East, Victoria, Australia, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'M905' and distinguish the new *Argyranthemum* as a new and distinct cultivar:

1. Compact, upright and rounded plant habit.
2. Freely branching habit, dense and bushy plants.
3. Freely flowering habit with numerous inflorescences per plant.

4. Anemone-type inflorescences with pink-colored ray florets and yellow-colored disc florets.

Plants of the new *Argyranthemum* differ from plants of the female parent, the selection M2/16, in the following characteristics:

1. Plants of the new *Argyranthemum* are more compact than plants of the female parent selection.
2. Leaves of plants of the new *Argyranthemum* are more green in color than leaves of plants of the female parent selection.
3. Plants of the new *Argyranthemum* and the female parent selection differ in ray floret coloration.

Plants of the new *Argyranthemum* can be compared to plants of the cultivar M8/20, disclosed in U.S. Plant Pat. No. 13,218. In side-by-side comparisons conducted in Narre Warren East, Victoria, Australia, plants of the new *Argyranthemum* had broader leaves than plants of the cultivar M8/20. In addition, plants of the new *Argyranthemum* and the cultivar M8/20 differed in ray floret coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Argyranthemum.*

The photograph at the bottom of the sheet comprises a side perspective view of a typical flowering plant of 'M905' grown in a container.

The photograph at the top of the sheet comprises a close-up view of typical inflorescences of 'M905'.

DETAILED BOTANICAL DESCRIPTION

The aforementioned photographs, following observations and averaged measurements describe plants grown in Bonsall, Calif., in an outdoor nursery under full sunlight during the spring and summer with day temperatures averaging 24° C., night temperatures averaging 18° C. Plants had been growing for about four months when the photographs and description were taken. Color references are made to The Royal Horticultural Society Colour Chart, 1995 Edition, except where general terms of ordinary dictionary significance are used.

Botanical classification: *Argyranthemum frutescens* cultivar M905.

Parentage:

*Female, or seed, parent.*—Proprietary seedling selection of *Argyranthemum frutescens* identified as M2/16, not patented.

*Male, or pollen, parent.*—An unidentified seedling selection of *Argyranthemum frutescens,* not patented.

Propagation:

*Type.*—Terminal vegetative cuttings.

*Time to initiate roots, summer and winter.*—About one to two weeks at 22° C.

*Time to produce a rooted cutting, summer and winter.*—About one month at 20° C.

*Root description.*—Fibrous, fine; white in color.

*Rooting description.*—Freely branching.

Plant description:

*General appearance.*—Inverted triangle; compact, upright and rounded plant form with dense foliage and inflorescences held above and beyond the foliage. Moderately vigorous growth habit.

*Plant height.*—About 18 cm.

*Plant width.*—About 28 cm.

*Lateral branch description.*—Quantity per plant: About eight lateral branches. Length: About 17 cm. Diameter: About 3 mm. Internode length: About 7 mm. Aspect: Initially upright to outwardly spreading. Texture: Smooth, glabrous. Strength: Strong. Color: 145B.

*Foliage description.*—Arrangement: Alternate, simple. Length: About 2.6 cm. Width: About 2 cm. Shape: Pinnatifid, deeply and irregularly dissected. Apex: Acute. Base: Attenuate. Margin: Entire; deeply and finely dissected; sinuses parallel to divergent. Texture, upper and lower surfaces: Smooth, glabrous. Venation pattern: Pinnate. Petiole length: About 1.7 cm. Petiole diameter: About 2.5 mm. Petiole texture, upper and lower surfaces: Smooth, glabrous. Color: Developing and fully expanded foliage, upper and lower surfaces: 146A; venation, 146C. Developing and fully expanded foliage, lower surface: 146B; venation, 146C. Petiole, upper and lower surfaces: 146C.

Inflorescence description:

*Appearance.*—Anemone-type inflorescences with ligulate ray florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plant flower from spring to early fall in Southern California; plants flower continuous during this period.

*Inflorescence longevity.*—Inflorescences last about one week on the plant.

*Quantity of inflorescences.*—Freely flowering habit, about 20 to 24 open inflorescences and inflorescence buds per lateral branch.

*Fragrance.*—Sour.

*Inflorescence size.*—Diameter: About 3.2 cm. Depth (height): About 1.5 cm. Diameter of disc: About 1 cm. Receptacle height: About 8 mm. Receptacle diameter: About 1.1 cm.

*Inflorescence buds, at stage of showing color.*—Height: About 8 mm. Diameter: About 8 mm. Shape: Ovoid. Color: 155B.

*Ray florets.*—Quantity per inflorescence: About 28 outer ray florets in two whorls and about 24 smaller inner ray florets in a single whorl. Shape: Ligulate. Length: Outer ray florets, about 1.5 cm; inner ray florets, about 8 mm. Width: Outer ray florets, about 3 mm; inner ray florets, about 2 mm. Apex: Emarginate. Base: Acute. Margin: Entire. Texture, upper and lower surfaces: Smooth, glabrous; velvety. Aspect: Initially upright; with development, eventually horizontal to the peduncle. Color: When opening, upper surface: 155A. When opening, lower surface: 155D. Fully opened, upper surface: 70B to 70C; color becoming closer to 75D with development. Fully opened, lower surface: 75C.

*Disc florets.*—Arrangement: Massed at the center of the inflorescence. Quantity per inflorescence: About 90. Shape: Tubular, elongated; apex, five-pointed; base, fused. Length: About 5 mm. Diameter, apex: About 1 mm. Diameter, base: Less than 1 mm. Color: Immature: 13A. Mature, apex: 13B. Mature, midsection: 145C. Mature, base: 145D.

*Involucral bracts* (*phyllaries*).—Appearance: Scale-like; margins, papery. Quantity per inflorescence: About 30 in three whorls; imbricate. Length: About 3 mm. Width: About 1.5 mm. Shape: Elliptic. Apex: Acute. Base: Truncate. Margin: Entire. Texture, upper and lower surfaces: Smooth, glabrous. Color, upper surface: 145C. Color, lower surface: 144B to 144C.

*Peduncle.*—Strength: Moderately strong; wiry. Aspect: Upright to about 45° from vertical. Length, terminal inflorescence: About 4.3 cm. Length, second inflorescence: About 5.2 cm. Length, third inflorescence: About 3.7 cm. Diameter: About 1.5 mm. Texture: Smooth, glabrous. Color: 144A.

*Reproductive organs.*—Androecium: Only on disc florets. Stamen quantity per floret: Five. Anther length: Less than 1 mm. Anther shape: Oval. Anther color: 14A. Amount of pollen: Scarce. Pollen color: 14A. Gynoecium: Present on ray and disc florets. Pistil quantity per floret: One. Pistil length: About 6 mm. Stigma shape: Two-parted. Stigma color: 13A. Style length: About 3 mm. Style color: 145C. Ovary color: 157A.

*Seed/fruit.*—Seed and fruit production has not been observed.

Disease/pest resistance: Resistance to pathogens and pests common to *Argyranthemums* has not been observed on plants grown under commercial conditions.

Temperature/weather tolerance: Plants of the new *Argyranthemum* have been observed to be tolerant to rain, wind and to temperatures from about −2° C. to about 40° C.

It is claimed:

1. A new and distinct cultivar of *Argyranthemum* plant named 'M905', as illustrated and described.

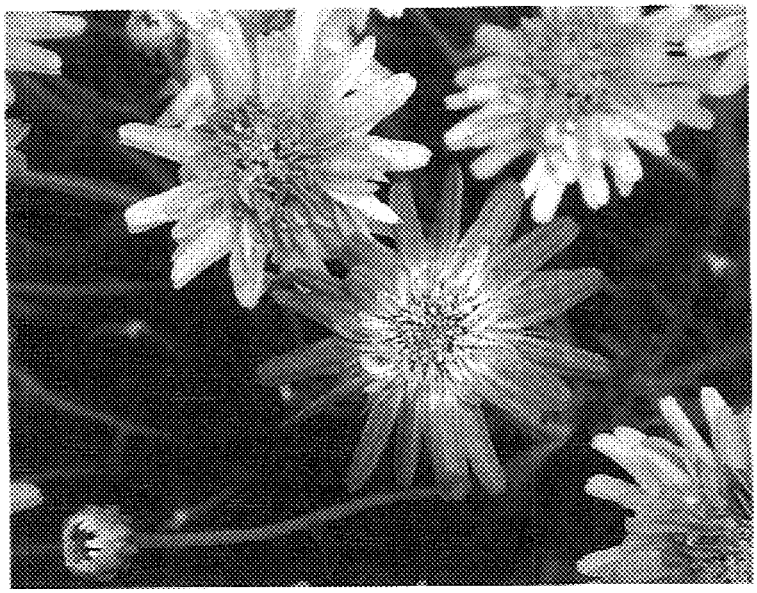
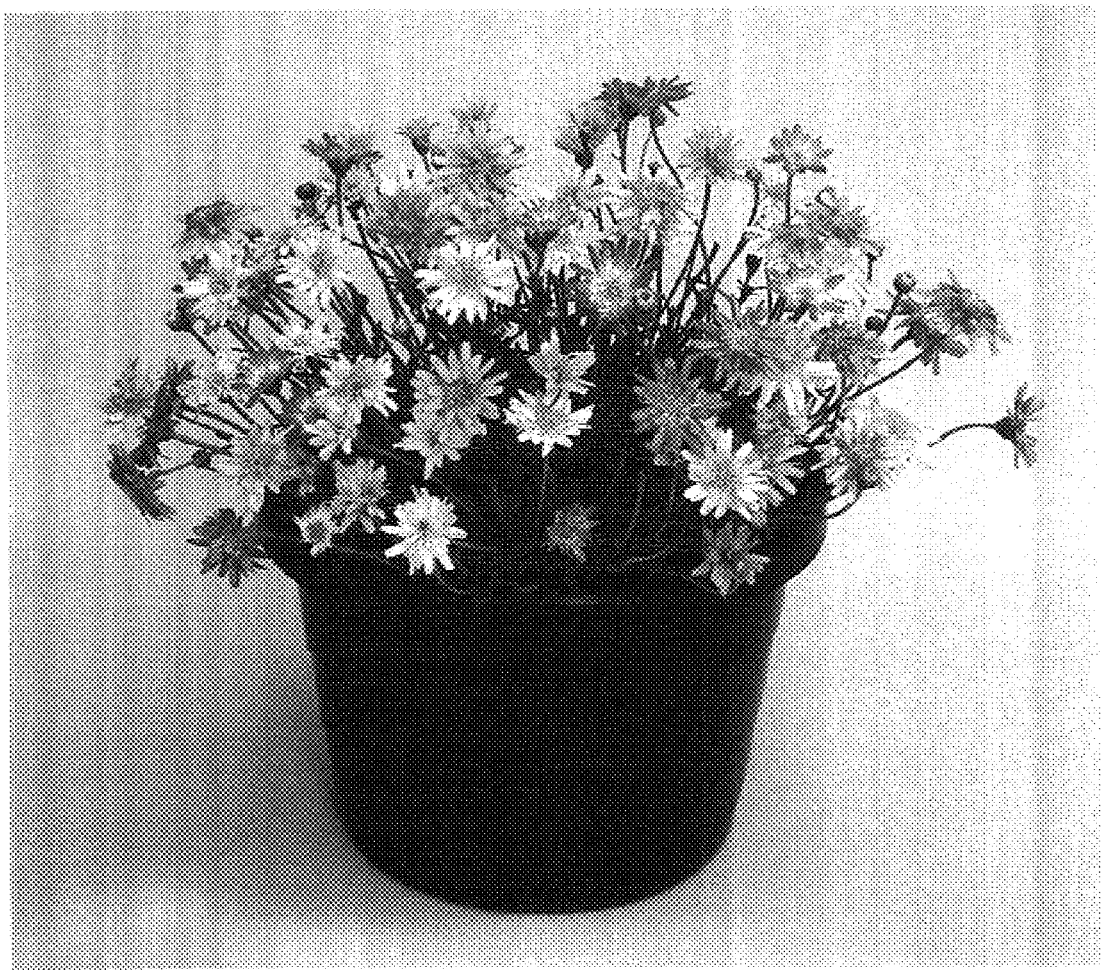

* * * * *